United States Patent [19]

Aikins et al.

[11] Patent Number: 5,159,073

[45] Date of Patent: Oct. 27, 1992

[54] INTERMEDIATES TO 1-CARBACEPHALOSPORINS AND PROCESS FOR PREPARATION THEREOF

[75] Inventors: James A. Aikins, Indianapolis; Eddie V. Tao, Carmel, both of Ind.

[73] Assignee: Eli Lilly and Company, Indianapolis, Ind.

[21] Appl. No.: 735,747

[22] Filed: Jul. 25, 1991

Related U.S. Application Data

[63] Continuation of Ser. No. 582,302, Sep. 13, 1990, abandoned.

[51] Int. Cl.$^5$ ............... C07D 205/85; C07D 405/06; C07D 307/54; C70B 35/02
[52] U.S. Cl. ........................... 540/364; 549/493
[58] Field of Search ........................... 540/364

[56] References Cited

U.S. PATENT DOCUMENTS

| | | | |
|---|---|---|---|
| 4,673,737 | 6/1987 | Evans et al. | 540/205 |
| 4,734,498 | 3/1988 | Cooper | 540/364 |
| 4,931,556 | 6/1990 | Boyer et al. | 540/364 |

OTHER PUBLICATIONS

Dane, Chem Ber 98, 789 (1965).
Sharma, Indian J Chem 2321 (1980).
Geiger, Peptides 3, pp. 1, 45.
Bose, Tetrahedron 37, 2321 (1980).
Gunda, Acta. Chem. Scand. 37B, 75 (1983).
Chauvette, J. Med Chem 18, 403 (1975).
March, Adv. Org. Chem 3rd Edition p. 693.
Hirai, Chemical Abstract, vol. 106, No. 5, p. 519, col. 1, 32 729t.
Minoru Hatanaka and Toshiyasu Ishimaru, "A Simple Synthesis of ($\pm$)-1-Carbacephem Derivatives", Tetrahedron Letters, vol. 24, No. 44, pp. 4837-4838 (1983).

*Primary Examiner*—Mark L. Berch
*Attorney, Agent, or Firm*—James J. Sales; Leroy Whitaker

[57] ABSTRACT

Disclosed is a process using hydrolysis and hydrogenation for converting enamino $\beta$-lactams to their saturated alkyl ester acid salts, key intermediates to 1-carbacephalosporins. Also disclosed are intermediates resulting from the process.

8 Claims, No Drawings

INTERMEDIATES TO 1-CARBACEPHALOSPORINS AND PROCESS FOR PREPARATION THEREOF

This application is a continuation of application Ser. No. 582,302, filed Sep. 13, 1990, now abandoned.

FIELD OF THE INVENTION

This invention generally relates to 1-carbacephalosporins and more particularly to intermediates to such compounds and processes for preparing those intermediates.

BACKGROUND OF THE INVENTION

Hashimoto et al. in U.S. Pat. No. 4,335,211, incorporated herein by reference, disclose a class of 1-carbacephalosporins having desirable antibiotic and oral activity characteristics. These compounds are currently being evaluated for the treatment of various conditions such as the common upper- and lower-respiratory tract infections caused by the pathogen *H. influenza*. One such compound, 7-(R)-phenylglycinamido-3-chloro-1-azabicyclo[4,2,0]oct-2-en-8-on-2-carboxylic acid, known as loracarbef or LY163892, has shown activity against a broad spectrum of bacteria in laboratory tests. Loracarbef has proven to be a relatively stable compound which exhibits high blood levels and a relatively long half life.

The 1-carbacephalosporins thus far have not been obtained from natural sources, for example, as microbial metabolites. Accordingly, methods for the total synthesis of these promising compounds and for intermediates to these compounds are highly desirable, particularly methods which are adaptable to large scale manufacture, provide good yields, and reduce the cost of manufacture More particularly desired key intermediates to such compounds have the formula

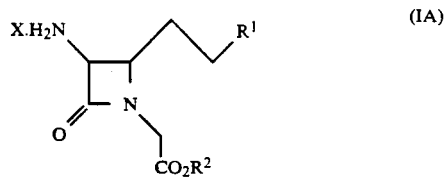

wherein $R^1$ is 2-furyl, phenyl, substituted phenyl, carboxy or protected carboxy, $R^2$ is $C_1$–$C_6$ alkyls, hydrogen, or a carboxy protecting group and X is an acid capable of forming acid addition salts. These intermediates represented by formula (IA) can then be further synthesized to form 1-carbacephalosporins, as disclosed generally in Evans et al., U.S. Pat. No. 4,665,171, incorporated herein by reference.

A particular compound represented by formula (IA), a saturated methyl ester oxalate (IB), may be formed by a process as follows in Scheme 1.

Scheme 1

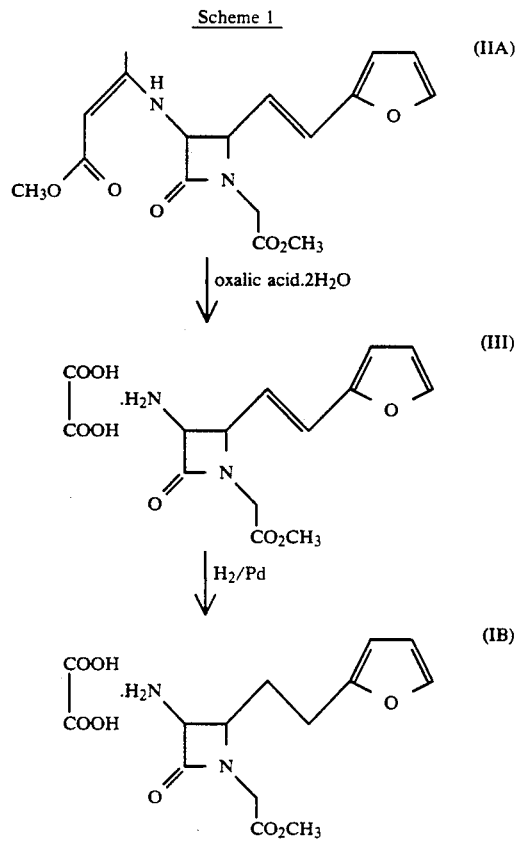

The process in Scheme 1 has approximately a 24 hour cycle time due, at least in part, to a relatively slow filtration of the compound as represented by formula (IB). Also, the intermediate represented by formula (III) is isolated before the ensuing hydrogenation step, and this also adds to the cycle time. Further, the process in Scheme 1 provides yields of the compound as represented by formula (IB) of approximately 20%. This relatively low yield may be due to ring cleavage and more particularly cleavage of the azetidinone ring resulting in an undesired compound having the formula

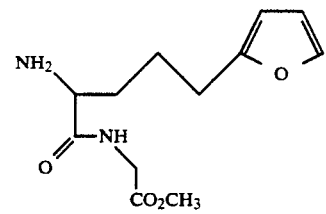

SUMMARY OF THE INVENTION

An object therefore is to provide a new and improved process for preparation of 1-carbacephalosporins and more particularly to a process for preparation of intermediates to 1-carbacephalosporins, and to novel intermediates.

The present invention provides a process for preparing a compound of the formula

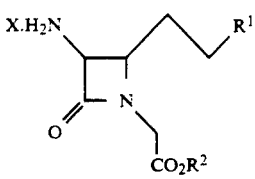

where $R^1$ is 2-furyl, phenyl, substituted phenyl, carboxy or protected carboxy, $R^2$ is a $C_1-C_6$ alkyl, hydrogen or a carboxy protecting group, and X is an acid capable of forming acid addition salts, and which includes the steps of hydrogenating a compound of the formula

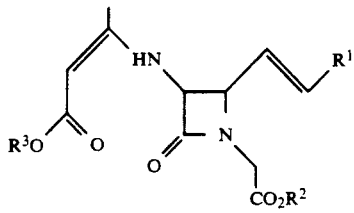

where $R^1$ and $R^2$ are defined as above and $R^3$ is hydrogen, a $C_1-C_6$ alkyl or a carboxy protecting group, to form a compound having the formula

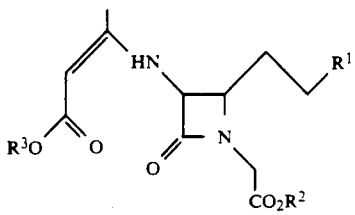

where $R^1$, $R^2$, and $R^3$ are defined as above and thereafter reacting the compound of formula (IVA) with an acid as defined by X.

The present invention also provides novel intermediate compounds represented by formula (IVA).

While the entire scope of process variables taught herein are believed operable, the present process and intermediates do have exemplary aspects. Exemplary compounds of the above formulas are those in which $R^1$ is 2-furyl, $R^2$ is methyl, $R^3$ is methyl, and X is oxalic acid.

Other objects and advantages will become apparent from the following description of the invention.

DETAILED DESCRIPTION OF THE INVENTION

The invention, together with its objects and advantages thereof, may be best understood by reference to the following description. However, it should be understood that the invention may be embodied in other specific forms without departing from the spirit or central characteristics thereof The present examples and embodiments therefore are to be considered in all respects as illustrative and not restrictive and the invention is not to be limited to the details given herein.

The term "substituted phenyl" specifies a phenyl group substituted with one or more moieties chosen from the group consisting of halogen, hydroxy, protected hydroxy, cyano, nitro, $C_1-C_6$ alkyl, $C_1-C_4$ alkoxy, carboxy, protected carboxy, carboxymethyl, protected carboxymethyl, hydroxymethyl, protected hydroxymethyl, amino, protected amino, aminomethyl, protected aminomethyl, trifluoromethyl, or N-(methylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di-(hydroxy)phenyl group such as 4-hydroxyphenyl, 3-hydroxyphenyl, 2,4-dihyroxyphenyl, the protected-hydroxy derivatives thereof and the like; a nitrophenyl group such as 3- or 4-nitrophenyl; a cyanophenyl group, for example 4-cyanophenyl; a mono- or di(lower alkyl)-phenyl group such as 4-methylphenyl, 2,4-dimethylphenyl, 2-methylphenyl, 4-(isopropyl)phenyl, 4-ethylphenyl, 3-(n-propyl)phenyl and the like; a mono-or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

The term "carboxy-protecting group" as used in the specification refers to one of the ester derivatives of the carboxylic acid group commonly employed to block or protect the carboxylic acid group while reactions are carried out on other functional groups on the compound Examples of such carboxylic acid protecting groups include 4-nitrobenzyl, 4-methylbenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the azetidinone ring and can be removed at the appropriate point without disrupting the remainder of the molecule. (Such harsh removal conditions are also to be avoided when removing amino-protecting groups and hydroxy-protecting groups.) A preferred carboxylic acid protecting group is the allyl group. Similar carboxy-protecting groups used in the cephalosporin, penicillin and peptide arts can also be used to protect a carboxy group substituents of the azetidinone. Further examples of these groups are found in E. Haslam, "Protective Groups in Organic Chemistry", J.G.W. McOmie, Ed., Plenum Press, New York, N.Y., 1973, Chapter 5, and T.W. Greene, "Protective Groups in Organic Synthesis", John Wiley and Sons, New York, N.Y., 1981, Chapter 5. The related terms "protected carboxy" and "protected carboxymethyl" denote that a carboxy group is substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups and the like.

Further examples of hydroxy-protecting groups are described by C.B. Reese and E. Haslam, "Protective Groups in Organic Chemistry", J.G.W. McOmie, Ed., Plenum Press, New York, N.Y., 1973, Chapters 3 and 4, respectively, and T.W.Greene, "Protective Groups in Organic Synthesis", John Wiley and Sons, New York, N.Y., 1981, Chapters 2 and 3. Some preferred hydroxy-protecting groups are the trityl group and the tetrahydropyranyl group. The related terms "protected hydroxy" and "protected hydroxymethyl" denote that a hydroxy group is bonded to one of the above hydroxy-protecting groups.

The term "amino-protecting group" refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl,1,1-diphenylprop-1-yloxycarbonyl, 2-phenylprop-2-yloxycarbonyl, 2-(p-toluyl)prop-2yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. Preferred amino-protecting groups are the allyloxycarbonyl, the t-butoxycarbonyl, and the trityl groups. Similar amino-protecting groups used in the cephalosporin, penicillin and peptide art are also embraced by the above terms Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7 The related terms "protected amino" and "protected aminomethyl" denote that an amino group is substituted with an amino-protecting group discussed above.

The present invention provides a process for the preparation of intermediates to 1-carbacephalosporin following Scheme 2.

Scheme 2

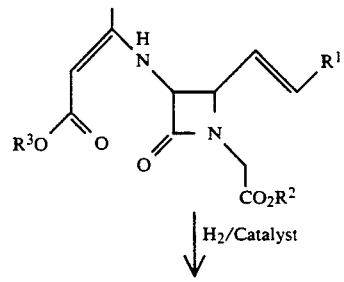

(IIB)

↓ $H_2$/Catalyst

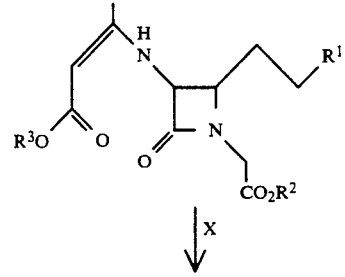

(IVA)

↓ X

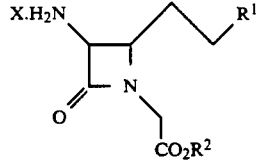

(IA)

wherein $R^1$ is 2-furyl, phenyl, substituted phenyl, carboxy or protected carboxy, $R^2$ is a $C_1$-$C_6$ alkyl, hydrogen or a carboxy protecting group, $R^3$ is hydrogen, a $C_1$-$C_6$ alkyl or a carboxy protecting group, and X is an acid capable of forming acid addition salts. More preferably, $R^2$ is a $C_1$-$C_6$ alkyl or a carboxy protecting group and $R^3$ is a $C_1$-$C_6$ alkyl or a carboxy protecting group.

The starting compounds as represented by formula (IIB), enamino β-lactams, are readily prepared by prior art processes. For example, Bose, Pat. No. 4,260,743, incorporated herein by reference, teaches synthesis of compounds generally of the configuration of formula (IIB), by activating the carboxyl group of a vinylamino salt of the formula

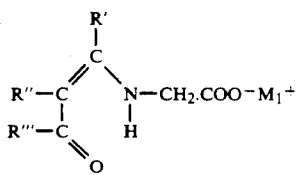

wherein R' represents lower alkyl, aryl or aryl(loweralkyl), R" represents hydrogen or lower alkyl or R' and R" together with the carbon atom to which they are attached represent lower cycloalkyl and R'" represents a lower alkyl or a group —OR, wherein R represents lower alkyl, and wherein $M_1+$ is the cation of a base, with an appropriate activating agent and reacting the activated compound in the presence of a tertiary base with an imino compound (Schiff's base) of the formula

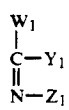

wherein $W_1$, $Y_1$, and $Z_1$ are hydrogen or selected organic radicals, using, however, the following Schiff's base

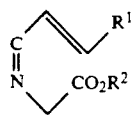

wherein $R^1$ and $R^2$ are defined as previously.

The hydrogenation in the present invention takes place in the presence of a standard hydrogenation catalyst. Hydrogenation catalysts include nickel, platinum, rhodium, ruthenium, copper chromite, iridium, osmium, palladium, and combinations thereof. An exemplary catalyst is a supported palladium, e.g., 5% or 10% palladium on carbon, barium carbonate, or other suitable support. The reduction generally is carried out at atmospheric conditions or at somewhat elevated pressures, and at substantially room temperature.

The intermediate represented by formula (IVA) is then reacted with an acid capable of forming acid addition salts such as the desired compound of formula (IA). Acids employed to form the addition salts must be relatively strong, and preferably have pKa values of about 2 or less. Such acids include inorganic acids such as hydrochloric acid, hydrobromic acid, hydroiodic acid, sulfuric acid, phosphoric acid, and the like, and organic acids such as maleic, p-toluenesulfonic, methanesulfonic acid, oxalic acid, p-bromophenylsulfonic acid, halogenated acetic acid, and the like. Preferably, the acid is oxalic acid or oxalic acid dihydrate.

Polar organic cosolvents may be used as precipitants to remove starting material and for isolating and cleanup. One such precipitant is acetonitrile.

The process of the invention is a "one-pot", two-step process and avoids the need to isolate an intermediate, which affords savings in time, equipment and man hours in manufacturing the key intermediate represented by formula (IA). Further, the filtration of the compound represented by formula (IA) is carried out relatively quickly, which aids in reducing overall cycle time relative to the prior art process. Also, the yield provided by the process of the invention is substantially higher than that of the process in Scheme 1 herein described.

The following examples further illustrate the specific aspects of the present invention. The examples are not intended to be limiting in any respect and should not be so construed.

EXPERIMENTAL SECTION

The starting material for the experiments illustrating the invention has the formula

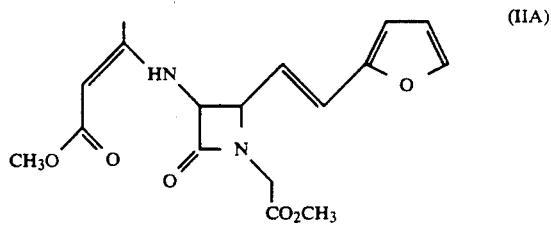

while the intermediate formed after hydrogenation has the formula

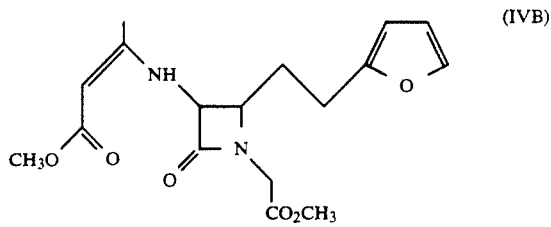

and the key intermediate formed has the formula

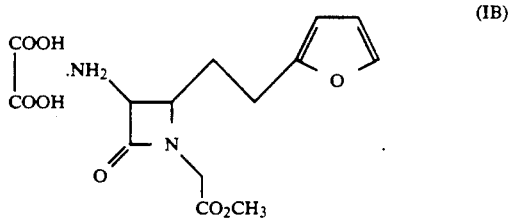

EXAMPLE 1

An 89.09 gram sample of the compound represented by formula (IIA) was added to 0.8 gram of 5% palladium on carbon. The mixture was then subjected to a hydrogen atmosphere at 20 psi and at room temperature for three hours and twenty minutes. HPLC indicated very little starting material after the hydrogenation. The palladium catalyst was removed by filtration, and the mixture was placed in a rotary evaporator at a temperature of about 25°–40° C. to concentrate the mixture to an oil. To the mixture, 350 ml of acetonitrile, 16.6 grams of oxalic acid, and 1 ml of water was added and the mixture was stirred for two and one-half hours. The mixture was chilled to 0°-5° C., then filtered. The cake was washed with 500 ml of acetonitrile. The precipitate was dried in a vacuum at a temperature of approximately 40° C.

The dried precipitate had a mass of 19.42 grams which represented a percent weight yield of 61.6% of the theoretical mass (31.5 grams). The purity indicated by HPLC of the above precipitate was 95.7% of the compound of formula (IB), resulting in a corrected yield of 59%.

EXAMPLE 2

To 0.10 liters of the compound of formula (IIA), 1.64 grams of 5% palladium on carbon was added. The mixture was hydrogenated at 20 psi and at room temperature for three hours At that time, HPLC indicated that 29% of the starting material was still left. Therefore, the mixture was refrigerated overnight after which hydrogenation was continued for another four and one-half hours at which time HPLC indicated no starting material present. The palladium catalyst was then removed by filtration and the mixture washed with 75 ml of methylene chloride. The mixture was concentrated to an oil by heating in a rotary evaporator at a temperature of about 25°–40° C. To the mixture, 650 ml of acetonitrile and 21.4 grams of oxalic acid dihydrate were added. The mixture was stirred for two hours and then chilled to 0°–5° C. The precipitate was then filtered and washed with 800 ml of acetonitrile and the precipitate was dried in vacuo. The mass of the resulting precipitate (compound of formula (IB)) was 38.13 grams and had a percent weight yield of 65.7% of theory, (58.06 grams).

It is noteworthy that the compound of the following formula

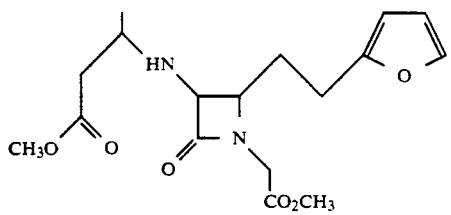

(V)

was not produced in the hydrogenation step in either of the examples. This was a concern as production of a compound represented by formula (V) would be detrimental to further synthesis according to the invention because one would be left with a 3-alkylamino substituent which could not be readily converted to a useful 3-amino intermediate.

We claim:

1. A process for the preparation of compounds having the formula

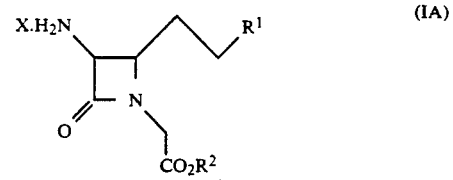

(IA)

wherein $R^1$ is 2-furyl, phenyl, substituted phenyl, carboxy or protected carboxy, $R^2$ is hydrogen, or a carboxy protecting group and X is an acid capable of forming acid addition salts, comprising the steps of:
  hydrogenating a compound of the formula

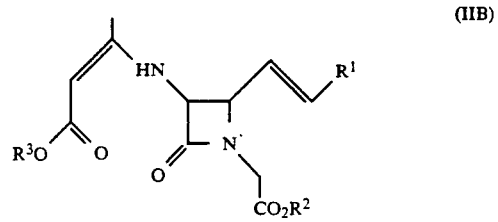

(IIB)

wherein $R^1$ and $R^2$ are defined as above and $R^3$ is hydrogen, or a carboxy protecting group,
in the presence of a hydrogenation catalyst, to form a compound having the formula

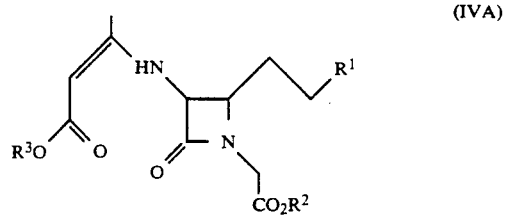

(IVA)

wherein $R^1$, $R^2$, and $R^3$ are defined as above and thereafter reacting the compound of formula (IVA) with an acid as defined by X.

2. The process as recited in claim 1 wherein $R^1$ is 2-furyl.

3. The process as recited in claim 1 wherein $R^2$ is methyl.

4. The process as recited in claim 1 wherein $R^3$ is methyl.

5. The process as recited in claim 1 wherein X is oxalic acid or oxalic acid dihydrate.

6. The process as recited in claim 5 wherein $R^1$ is 2-furyl, $R^2$ is methyl, $R^3$ is methyl and X is oxalic acid.

7. The process as recited in claim 6 wherein said hydrogenation catalyst is a palladium catalyst.

8. The process as recited in claim 1 wherein $R^2$ is a carboxy protecting group and $R^3$ is a carboxy protecting group.

* * * * *